United States Patent [19]

Horbaschek

[11] Patent Number: 5,509,044

[45] Date of Patent: Apr. 16, 1996

[54] MEDICAL DIAGNOSTICS SYSTEM HAVING OPTIMIZED SIGNAL ACQUISITION FOR RADIATION EXPOSURE CONTROL

[75] Inventor: Heinz Horbaschek, Erlangen, Germany

[73] Assignee: Siemens Aktiengesellschaft, Munich, Germany

[21] Appl. No.: 427,838

[22] Filed: Apr. 26, 1995

Related U.S. Application Data

[63] Continuation of Ser. No. 120,812, Sep. 15, 1993.

[30] Foreign Application Priority Data

Oct. 1, 1992 [DE] Germany .................. 42 32 901.9

[51] Int. Cl.[6] .................................................. H05G 1/64
[52] U.S. Cl. ........................... 378/97; 378/98.7; 378/108
[58] Field of Search ........................ 378/97, 108, 98.7

[56] References Cited

U.S. PATENT DOCUMENTS

| | | | |
|---|---|---|---|
| 2,796,527 | 6/1957 | Oosterkamp | 378/97 |
| 4,097,741 | 6/1978 | Pfeiler et al. | 378/97 |
| 4,309,613 | 1/1982 | Brunn et al. | |
| 4,360,731 | 11/1982 | Fink et al. | 378/108 |
| 4,400,823 | 8/1983 | Haendle | |
| 4,423,521 | 12/1983 | Haendle et al. | |
| 4,455,669 | 6/1984 | Aichinger et al. | |
| 4,517,594 | 5/1985 | Horbaschek | |
| 4,674,108 | 6/1987 | Asahina et al. | |
| 4,935,946 | 6/1990 | Hefter et al. | |
| 5,029,338 | 7/1991 | Aichinger et al. | |
| 5,048,067 | 9/1991 | Horbaschek | |
| 5,050,198 | 9/1991 | Honda | |
| 5,062,129 | 10/1991 | Mulder | 378/97 |
| 5,148,460 | 9/1992 | Aichinger | |

FOREIGN PATENT DOCUMENTS

| | | |
|---|---|---|
| 2135205 | 2/1973 | Germany . |
| 3741760 | 6/1989 | Germany . |
| 4017597 | 12/1991 | Germany . |
| 2174492 | 11/1986 | United Kingdom . |

*Primary Examiner*—Craig E. Church
*Attorney, Agent, or Firm*—Hill, Steadman & Simpson

[57] ABSTRACT

A medical radiological diagnostics system having an automatic exposure unit employs signal acquisition and a processing circuitry for controlling the radiation source so as to obtain easily diagnosed exposures with a low radiation load. This is accomplished by disposing a stray radiation grid between the radiation receiver and a radiation sensor, or by selecting the spacing between the radiation receiver and the radiation sensor such that scattered radiation is not incident on the radiation sensor, or, in a system having an x-ray image intensifier and a light sensor, by supplying the output signal of the light sensor to the control circuit through a high-pass filter. In all versions, the measured signal is not disadvantageously influenced by scattered radiation, so that a correct exposure of x-ray film is possible.

6 Claims, 4 Drawing Sheets

MEDICAL DIAGNOSTICS SYSTEM HAVING OPTIMIZED SIGNAL ACQUISITION FOR RADIATION EXPOSURE CONTROL

This is a continuation of application Ser. No. 08/120,812, filed Sep. 15, 1993.

BACKGROUND OF THE INVENTION

1. Field of the Invention

The present invention is directed to a medical diagnostics system wherein a subject is irradiated with x-rays to produce an image, of the type having means for automatically controlling the exposure.

2. Description of the Prior Art

An x-ray diagnostics unit having an automatic exposure unit for measuring the dose rate and thereby controlling an adjustment element for the x-ray tube voltage is disclosed by German OS 21 35 205. In this known system, an x-ray radiator produces an x-ray shadowgraph on an x-ray film of an examination subject arranged between the x-ray film and the x-ray tube. The x-radiation that penetrates through the x-ray film is incident on a measuring chamber of an automatic exposure unit that ends the exposure after a defined radiation dose has been reached.

German OS 31 06 627 discloses an x-ray diagnostics system having a control circuit for controlling the exposure. In this x-ray diagnostics system, an image intensifier video chain receives the radiation that is emitted by a radiation transmitter and penetrates through an examination subject, this radiation being converted into a visible image of the examination subject. The image intensifier video chain includes an image intensifier with a video pick up tube coupled thereto by an optical coupling element, a video intensifier and a monitor.

The control circuit for controlling the exposure includes circuitry for forming a control voltage for the dose rate of the x-ray tube. A rated value generator and a circuit that contains an evaluation circuit and means for the blanking of parts of the video signal in order to form a dominant field are connected to the control circuit. An actual value generator is connected to the photo-cathode of the x-ray image intensifier and to the high-voltage generator thereof. The actual value generator supplies, the control circuit with an actual value signal that corresponds to the average image brightness. The actual value signal, the rated value signal and the output signal of the circuit are superimposed on one another in the control circuit as a correction value of the rated value.

An x-ray diagnostics unit having an x-ray image intensifier video chain is disclosed by German OS 32 25 061. A video camera is coupled to the x-ray image intensifier via optics having a base objective and a camera objective. A mirror that couples a part of the light stream onto a light detector, composed of a matrix of photo-sensors, lies in the optical beam path. The parallel outputs the photo-sensors are connected via switches to a summing amplifier of a test circuit, which includes means for setting the rated value. The output of the test circuit regulates a high-voltage generator of an x-ray radiator. Any desired part of the x-ray image can be selected by the switches as a measurement dominant, or a plurality of parts can also be interconnected. Regions of the measuring dominant can be differently weighted via variable resistors that follow the photo-sensors. An integration of their signals can ensue via amplifiers and capacitors that follow the photo sensors. A peak weighing of these signals is enabled when a respective diode is connected between the amplifiers and the capacitors.

In these known exposure controls, the control of the x-ray radiator ensues by regulating operation of the x-ray radiator to achieve a defined blackening of an x-ray film within a predetermined measuring dominant. The signal acquired by the radiation sensor within the measuring dominant, however, is not only disadvantageously influenced by the primary radiation, but also by the scattered radiation and, particularly if an x-ray image intensifier video chain is used as the radiation receiver, by the low frequency drop (LFD). The low frequency drop arises due to the rough contrast behavior of the x-ray image intensifier. The rough contrast behavior of the x-ray image intensifier is expressed by a defined drop of the modulation transfer function (MTF), even given extremely low spatial frequencies. This undesired effect is caused, for example, by reflections in the x-ray image intensifier and, given a transparency discontinuity in the examination subject, causes the corresponding brightness discontinuity at the output luminescent screen of the x-ray image intensifier to appear blurred or spread. Given the presence of direct radiation, i.e. extremely high radiation intensities next to the subject region of interest, a large part of the "bright" region thus extends into the normally exposed region, corresponding to a differential auxiliary exposure with information-free steady radiation. When, as is usual in practice, the measurement dominant of the automatic exposure unit lies in the region of interest, then the dose rate is regulated down to the rated value of the brightness due to the light level raised by the LFD component. By contrast to the absence of direct radiation, however, this means that less of a dose rate is applied and thus greater quantum noise also appears.

SUMMARY OF THE INVENTION

It is an object of the present invention to implement a medical radiological diagnostics system of the type having an automatic exposure unit wherein the signal acquisition and signal processing for controlling the radiation transmitter are improved in comparison to known systems in order to obtain easily diagnosed exposures given a low radiation load.

In a first version of the invention, this object is achieved by disposing a stray radiation grid between the radiation receiver and the radiation sensor.

In another embodiment version of the invention, the object is achieved by selecting the spacing between the radiation receiver and the radiation sensor such that scattered radiation is no longer incident on the radiation sensor.

An advantage of both of these embodiment is that the scattered radiation no longer disadvantageously influences the signal of the radiation sensor, so that properly exposed, and thus easily diagnosed, exposures of an examination subject can be produced with a low radiation load.

In a third embodiment of the invention, having an x-ray image intensifier and a light sensor, the object is achieved by supplying the output signal of the light sensor to the control circuit via a high-pass filter.

An advantage of this embodiment is that the signal components caused by the rough contrast behavior of the image intensifier are filtered out by the high-pass filter and thus no longer disadvantageously influence the exposure control.

In a fourth embodiment of the invention, the object is achieved by employing a second light sensor implemented as a matrix sensor following the image intensifier, the signals of this second light sensor being supplied to a matrix memory. A first circuit arrangement for electrical simulation of a dominant and a second circuit arrangement for generating an arbitrarily selectable dominant follow the matrix memory. The signals of the first and second circuit arrangements are supplied to a difference forming element that acts on the rated value signal.

An advantage of all embodiments of the invention is that the measured signal is no longer disadvantageously influenced by scattered radiation, so that a correct exposure of an x-ray film is possible. In systems with an x-ray image intensifier video chain, the control of the radiation transmitter ensues at a constant quantum noise ratio without the influencing by the rough contrast behavior, so that easily interpretable exposures are obtained. Since the control of the radiation dose within a measuring dominant ensues such that the quantum noise ratio is constant, this leads to a general reduction of the set dose, so that the radiation load on the examination subject is slight.

DESCRIPTION OF THE PREFERRED EMBODIMENTS

Figure 1:
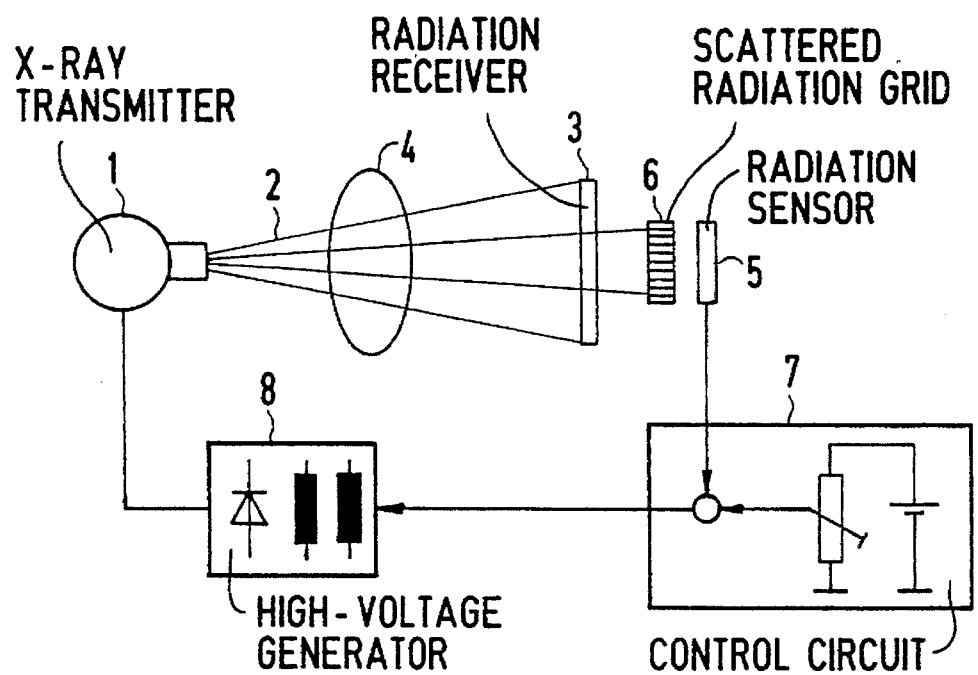
FIG. 1 is a schematic block diagram of a first embodiment of a medical radiological diagnostics installation constructed in accordance with the principles of the present invention employing a scattered radiation grid and a radiation sensor.
Figure 6:
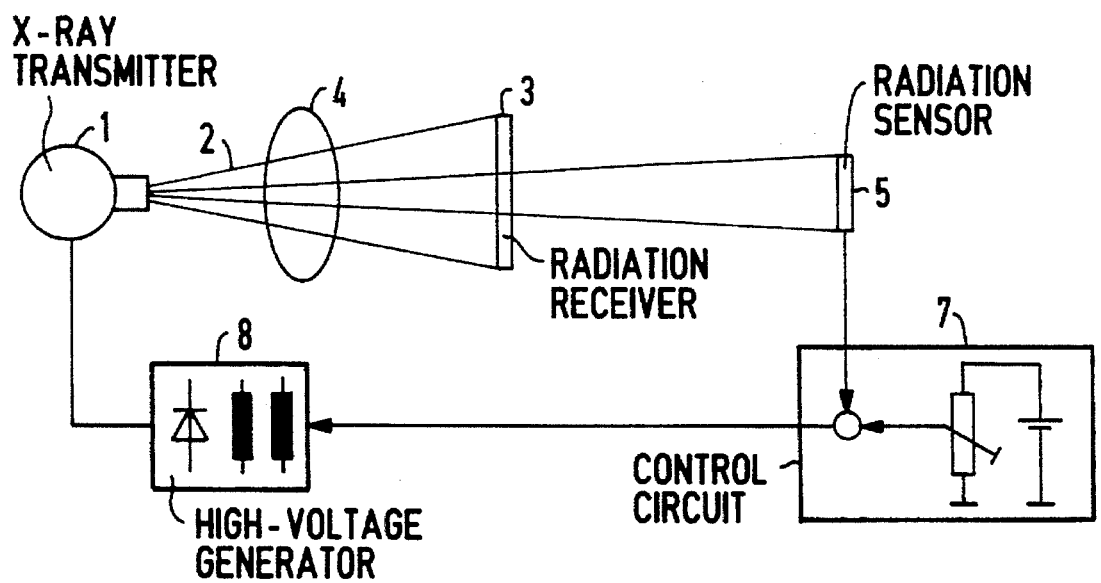
FIG. 6 is a schematic block diagram of a fifth embodiment of a medical radiological diagnostics installation constructed in accordance with the principles of the present invention, wherein the distance between the radiation receiver and the radiation sensor is sufficiently long so that no scattered radiation is incident on the radiation sensor.

FIG. 1 shows a medical diagnostics system having a radiation transmitter 1 whose ray beam 2 penetrates an examination subject 4 arranged between the radiation transmitter 1 and a radiation receiver 3. According to a first version of the invention, a scattered radiation grid 6 for the absorption of scattered radiation is arranged between a radiation sensor 5 and the radiation receiver 3. According to a version of the invention shown in FIG. 6, the distance between the radiation receiver 3 and the radiation sensor 5 is selected of such a size that scattered radiation is not incident on the radiation sensor 5. The distance can correspond to three times the thickness of a subject under examination and can thus lie in the range from 0.2 through 0.9 m.

The signal of the radiation sensor 5 is supplied to a control circuit 7, which generates an output signal, which is supplied to a generator 8 for controlling the energy supply of the radiation transmitter 1, on the basis of a comparison of the actual value of the signal of the radiation sensor 5 to a prescribable rated value. In this arrangement, the KV-dependent absorption of the radiation receiver 3 that, for example, is composed of an x-ray intensifier foil and of an x-ray film, is taken into consideration. This can ensue, for example, on the basis of an appropriate correction value. The arrangement of the invention thus achieves an exposure control that ensues independently of the scattered radiation, and is dependent only on the primary radiation component in the measuring dominant.

Figure 2:
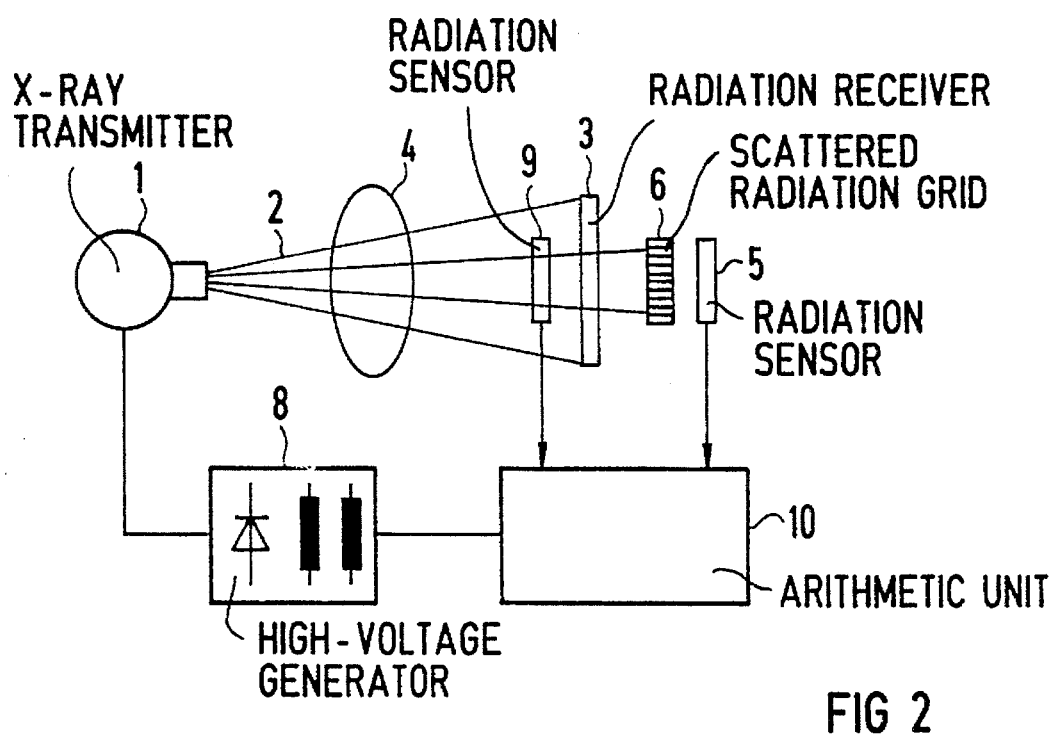
FIG. 2 is a schematic block diagram of a second embodiment of a medical radiological diagnostics installation constructed in accordance with the principles of the present invention, employing a scattered radiation grid and two radiation sensors.

FIG. 2 shows another version of a medical diagnostic system of the invention, wherein elements that have already been given a reference character in FIG. 1 are identified with the same reference character. Differing from the exemplary embodiment of FIG. 1, the embodiment of FIG. 2 employs a second radiation sensor 9, whose signal is supplied together with the signal of the first radiation sensor 5 to an arithmetic unit 10. The second radiation sensor 9 precedes the radiation receiver 3 in the radiation propagation direction. The first radiation sensor 5 supplies a signal which is essentially dependent only on the primary radiation, whereas the signal of the second radiation sensor 9 is essentially dependent on the primary radiation and on the scattered radiation. The arithmetic unit 10 forms the difference between the two signals, so that an output signal corresponding to the scattered radiation component is obtained. The drive of the radiation transmitter 1 for adjusting the dose ensues on the basis of this output signal, so that the quantum noise ratio is thus increased or kept constant.

Figure 3:
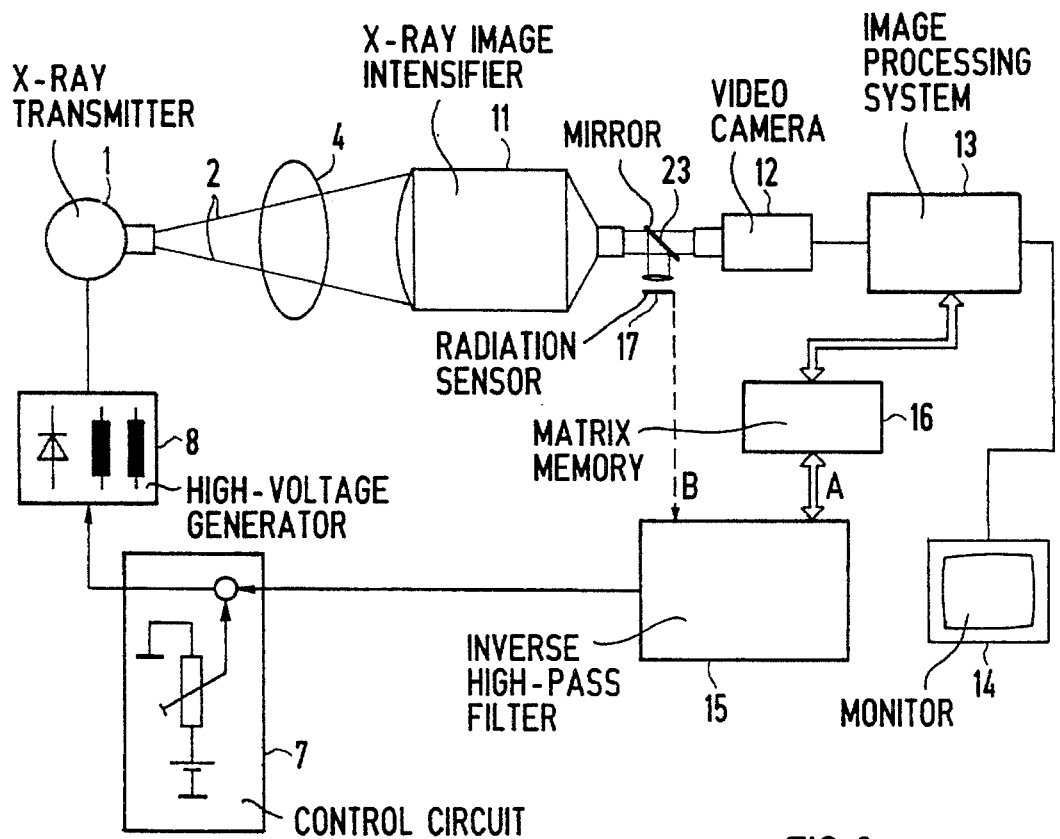
FIG. 3 is a schematic block diagram of a third exemplary embodiment of a medical radiological diagnostics installation constructed in accordance with the principles of the present invention, employing an image intensifier video chain as the radiation receiver.

FIG. 3 shows a third version of a medical diagnostics system, wherein, differing from the exemplary embodiments of FIGS. 1 and 2, the radiation receiver 3 is implemented as an image intensifier video chain. The ray beam 2 emitted by the radiation transmitter 1 thus penetrates the examination subject 4 and is incident onto the input luminescent screen of an image intensifier 11 that converts the radiation shadowgram of the examination subject 4 into a visible image at the output of the image intensifier 11. A video camera 12 is coupled to the output of the image intensifier 11 via optics. The output signals of the video camera 12 are supplied to an image processing system 13 for producing an image of the examination subject 4 on a monitor 14.

The dose control for single and for fluoroscopy ensues dependent on the brightness of the output image of the image intensifier 11 which, for example, is acquired by a matrix sensor or ensues dependent on the video signals of the video camera 12. The output signals of the matrix sensor or the video signals—as image signals—can thereby represent the entire output image or a part of the output image of the image intensifier 11 as the measuring dominant. As "actual value signals", these output signals are less influenced by the scattered radiation than by additional, undesired signal parts due to the rough contrast behavior of the image intensifier 11. In order to assure a satisfactory dose or dose rate, it is important to eliminate these signal parts from the actual value signal. Since the rough contrast behavior of image intensifiers 11, however, is fundamentally known, the possibility of implementing a LFD compensation by image processing with the assistance of the entire image arises. The LFD compensation ensues by using a high-pass filter having filtering behavior that is inverse relative to the low-pass characteristic of the rough contrast behavior, according to the principle of the "unsharp mask". The high-pass filtering subsequently ensues by subtracting an image (i.e., the image signals thereof) that is unsharpened in spatial frequency, i.e. is low-pass-filtered subtracted from an original image (i.e., the image signals thereof).

For compensating the image signal parts generated by the rough contrast behavior (LFD), the output signals of the high-pass filter that is inverse to the low-pass characteristic of the rough contrast behavior are supplied to the control circuit 7. The actual value signal is thus purged of signal parts produced by the rough contrast behavior.

The LFD compensation can thereby ensue on the basis of all image signals, or can also ensue on the basis of the signals of a reduced image matrix. A reduction of the signal parts generated by the rough contrast behavior can already also be accomplished by generating the image signals of an unsharpened image are with only a one-dimensional spatial frequency filtering (instead of two-dimensional filtering), which acts, for example, only in the horizontal direction.

The signal path identified with reference character A in FIG. 3 shows that image signals of the image intensifier video chain are supplied to a first matrix memory 16 having a matrix of, for example, $1000^2$ memory locations, that is connected to the high-pass filter 15. This first matrix memory 16 may have a reduced matrix of, for example, $100^2$ memory locations, but then the full detail sharpness of the output image is not acquired.

According to a signal path referenced B, a third radiation sensor 17 can be provided in another exemplary embodiment on which at least one part of the output light of the image intensifier 11 is deflected via a mirror. This arrangement is particularly employed when the output signals of the image intensifier video chain have extremely large signal differences. Large signal differences, for example, arise when radiation is incident on the input luminescent screen of the image intensifier 11 directly and, for example, is highly attenuated by dense subject regions. These large signal differences can lead to over-modulated image signals, so that a complete LFD compensation can no longer ensue. The third radiation sensor 17 should therefore only acquire a part of the output light of the image intensifier 11 and should thus not be over-driven. The third radiation sensor 17 may be implemented with a reduced matrix of radiation sensors, so that it acquires the entire range of dynamics of the output image. On the basis of the output signals of the third radiation sensor 17, the LFD compensation in the high-pass filter 15 can then ensue.

Figure 4:
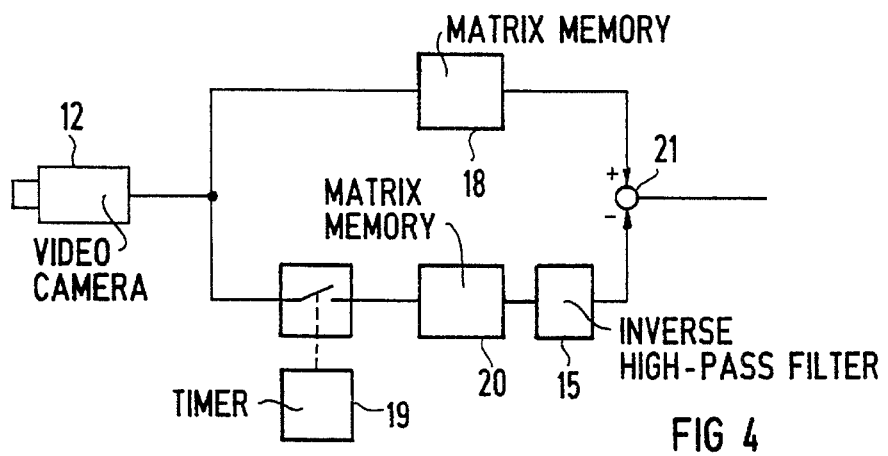
FIG. 4 is a schematic block diagram showing details of the video chain in the embodiment of FIG. 3.

The image processing means 13 can be formed by a circuit arrangement shown in FIG. 4. The image signals of the video camera 12 (which can also be executed as a matrix sensor) are supplied to a second matrix memory 18 and, controlled by a timer 19, are supplied at predetermined chronological intervals, i.e. in shutter mode, to a third matrix memory 20 such that only image signals free of over-modulation are stored. A LFD compensation of these image signals is achieved by supplying these signals to the high-pass filter 15 that is inverse to the LFD as shown in FIG. 4.

As shown in FIG. 4, the image signals of the second matrix memory 18 and the image signals of the third matrix memory 20 are supplied via the high-pass filter 15 inverse relative to the LFD to a subtractor 21 which is followed by the monitor 14. An LFD-compensated image can thus be produced.

Of course, the output signals of the subtractor 21 can also be supplied to the control circuits for dose regulation directly, instead of via the high-pass filter 15 and the matrix memory 16 shown in FIG. 3. The dose is thus also no longer controlled down given direct radiation incident on the image intensifier 11, which would deteriorate the quantum noise ratio. The dose applied in the region of interest of the examination subject 4 is thus independent of direct radiation in regions lying outside the measuring dominant that is incident on the image intensifier 11, since the LFD influences are no longer effective.

In addition to being implemented by high-pass filtering inverse to the LFD according to the principle of the "unsharp mask", LFD compensation can also be implemented via a modulation transfer function correction on the basis of Fourier transformation.

Figure 5:
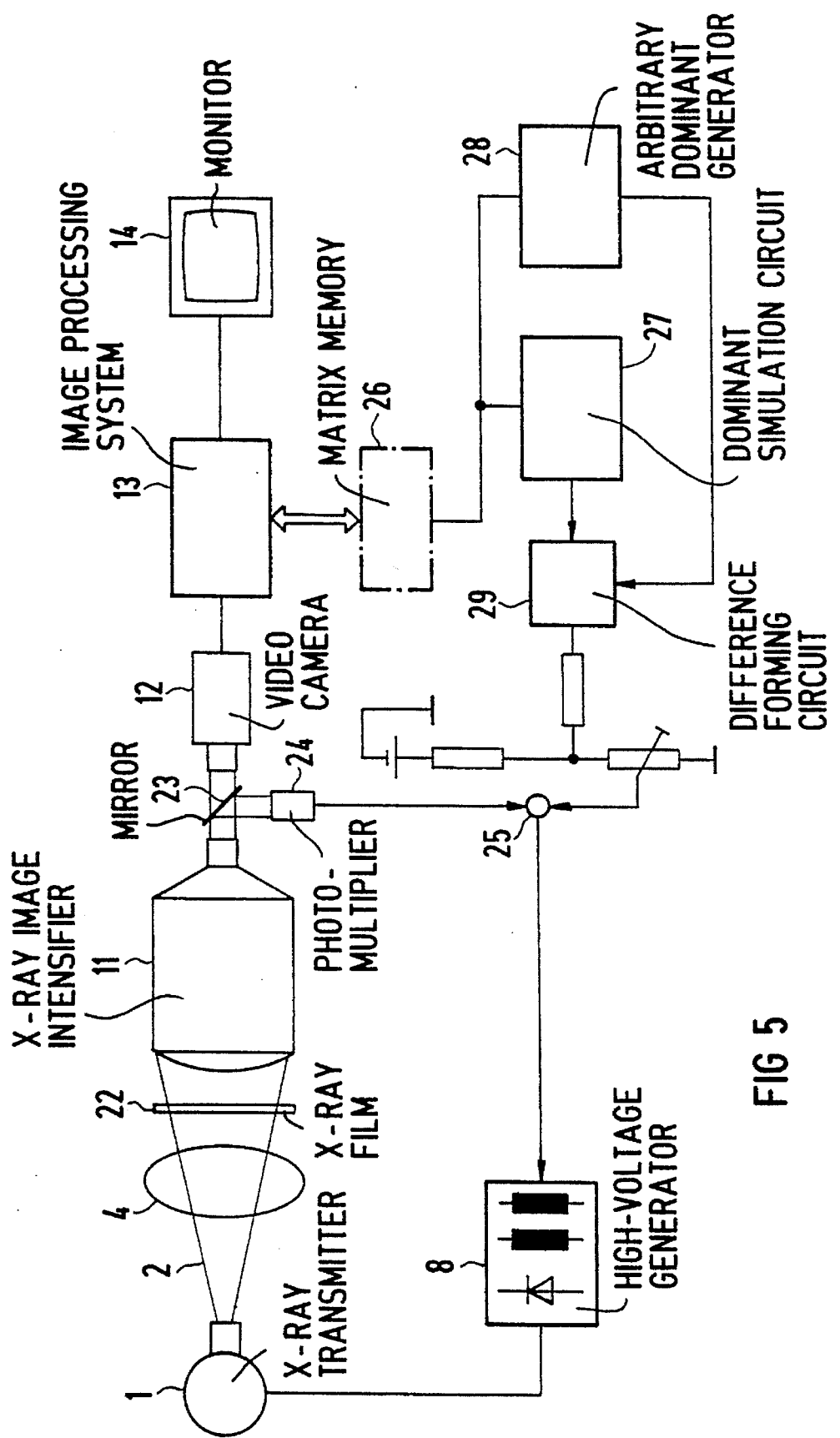
FIG. 5 is a schematic block diagram of a fourth exemplary embodiment of a medical radiological diagnostics installation constructed in accordance with the principles of the present invention employing a different version of an image intensifier video chain.

FIG. 5 shows a fourth exemplary embodiment of a medical diagnostics unit, whereby components already provided with reference characters in the preceding figures have the same reference characters. The ray beam penetrating the examination subject 4 is incident, for example, on x-ray film 22 that is arranged between the examination subject 4 and the following image intensifier 11. The output image of the image intensifier 11 is directed via an optics to the video camera 12 and via a mirror 23 onto a photomultiplier 24 that, for example, can be implemented as a matrix sensor.

The output signals of the individual matrix elements of the matrix sensor can be interconnected dependent on the desired measuring dominant. A matrix can also be produced by an LCD matrix shutter that is followed by a light sensor. Given such an LCD matrix shutter, individual regions can be switched to be light-transmissive, so that the desired measuring dominant can be produced.

The photomultiplier 24 (or the matrix sensor) covers a specific region of the output image of the image intensifier 11 and generates signals that are supplied to a comparator 25. Image signals of the image processing system 13 are supplied to a fourth matrix memory 26 while a target (or aiming) exposure is taking place, as is standard in x-ray image intensifier video systems. These image signals are then supplied to a first circuit arrangement 27 for electrical simulation of the measuring dominants and are supplied to a second circuit arrangement 28 for electrical generation of arbitrary measuring dominants. The output signals of the first and second circuit arrangements 27 and 28 are supplied to a difference-forming element 29 whose output signals act on a pre-settable rated value. The signal influenced by the output signals of the first and second circuit arrangements 27 and 28 are supplied to the comparator 25 which, based on the comparison to the actual value, delivers an output signal to the generator 8 for controlling the radiation transmitter 1 (x-ray radiator).

The possibility of arbitrary dominant formation can be applied given direct exposure, indirect exposure (cinema as well) as well as in an electronic immediate image. The LFD compensation, of course, is not necessary given x-ray film exposures unless the measurement of the exposure is undertaken via the image intensifier 11, as shown in FIG. 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical diagnostic system comprising:
    an x-ray transmitter;
    an x-ray image intensifier for receiving x-rays from said transmitter after passing through an examination subject, said x-ray image intensifier generating an optical image corresponding to an x-ray image of said examination subject;

a light sensor disposed in a path of said optical image, said light sensor generating an output signal;

control means supplied with said output signal of said light sensor for controlling the operation of said x-ray transmitter dependant on said output signal; and a high-pass filter connected between said light sensor and said control means through which said output signal passes.

2. A system as claimed in claim 1, wherein said light sensor comprises:

a matrix sensor which generates a plurality of output signals;

a first matrix memory to which said output signals of said matrix sensor are supplied;

a second matrix memory to which said output signals of said matrix sensor are supplied;

a high-pass filter connected at an output of said second matrix memory; and means for subtracting said output signals stored in said first matrix memory from the high-pass filtered output signals stored in said second memory, for supply to said control means.

3. A system as claimed in claim 2, further comprising means for supplying said output signals of said matrix sensor to said second matrix memory at predetermined time intervals.

4. A system as claimed in claim 2, wherein the respective matrices of said first and second matrix memories are identical.

5. A system as claimed in claim 2, wherein said second matrix memory has a matrix which is reduced in comparison to a matrix of said first matrix memory.

6. A medical diagnostic system comprising:

an x-ray transmitter;

an x-ray image intensifier disposed to receive x-rays from said x-ray transmitter after passing through an examination subject, said x-ray image intensifier generating an optical image corresponding to an x-ray image of said examination subject;

a first light sensor disposed in a path of said optical image, and generating a first output signal;

a second light sensor disposed in the path of said optical image in the form of a matrix sensor, and generating second output signals;

a matrix memory connected to said second light sensor for storing said second output signals;

first means following said matrix memory for electrically simulating a dominant image;

second means following said matrix memory for generating an arbitrarily selectable dominant image;

difference-forming means for forming a difference of signals from said first and second means;

means for superimposing said difference on a predetermined control signal; and control means, supplied with said difference superimposed on said predetermined control signal, for controlling the operation of said x-ray transmitter.

* * * * *